(12) United States Patent
Kumar

(10) Patent No.: US 9,526,544 B1
(45) Date of Patent: Dec. 27, 2016

(54) ANATOMICAL HUMERAL FIXATION SYSTEM AND METHOD

(71) Applicant: Avinash Kumar, Lakewood Ranch, FL (US)

(72) Inventor: Avinash Kumar, Lakewood Ranch, FL (US)

( * ) Notice: Subject to any disclaimer, the term of this patent is extended or adjusted under 35 U.S.C. 154(b) by 277 days.

(21) Appl. No.: 14/218,236

(22) Filed: Mar. 18, 2014

Related U.S. Application Data

(60) Provisional application No. 61/801,675, filed on Mar. 15, 2013.

(51) Int. Cl.
  *A61B 17/80* (2006.01)

(52) U.S. Cl.
  CPC .................................. *A61B 17/8061* (2013.01)

(58) Field of Classification Search
  CPC ...................................................... A61B 17/80
  USPC ..................................... 606/70, 71, 200–299
  See application file for complete search history.

(56) References Cited

U.S. PATENT DOCUMENTS

| | | | |
|---|---|---|---|
| 4,463,753 A | 8/1984 | Gustilo | |
| 8,535,313 B1* | 9/2013 | Masson | A61B 17/80 606/232 |
| 2009/0275947 A1* | 11/2009 | Graham | A61B 17/8061 606/71 |
| 2011/0218534 A1* | 9/2011 | Prandi | A61B 17/80 606/71 |
| 2013/0178905 A1* | 7/2013 | Graham | A61B 17/8085 606/282 |
| 2014/0214036 A1* | 7/2014 | Weiner | A61B 17/8004 606/71 |

* cited by examiner

*Primary Examiner* — Christopher Beccia
(74) *Attorney, Agent, or Firm* — Dinsmore & Shohl LLP

(57) ABSTRACT

An anatomical shoulder fixation system comprises a lower portion and an upper portion, the lower portion being a separate part and being coupled to the upper portion adjustably. For example, the relative position of the upper portion to the fixation system is capable of rotating and translating with relation to the lower part, accommodating placement on a shoulder even if displacement of the lesser tuberosity and the greater tuberosity due to fracture or dislocation. Examples include a flexible upper portion coupled to a lower portion or a more rigid upper portion joined to a lower portion, and combinations of these. In both examples, screws may be used to fix the lower portion prior to completing the displacement and fixation of the upper portion. For example, the lower portion may provide structures for attaching sutures, suitable for use with a curved needle shaft and suture.

12 Claims, 5 Drawing Sheets

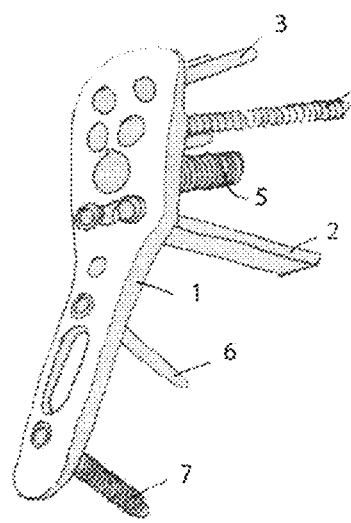
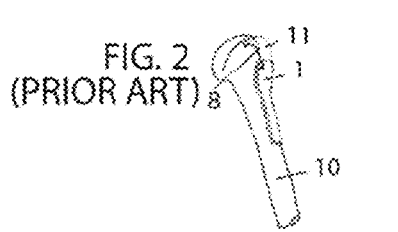
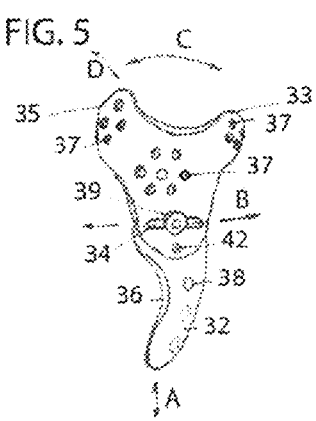
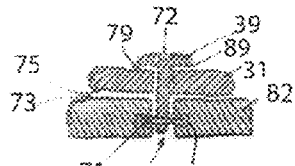
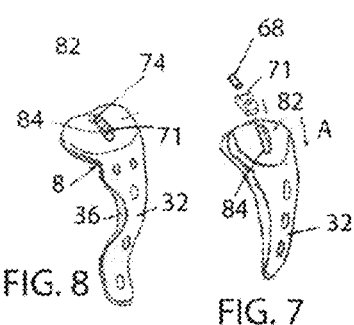
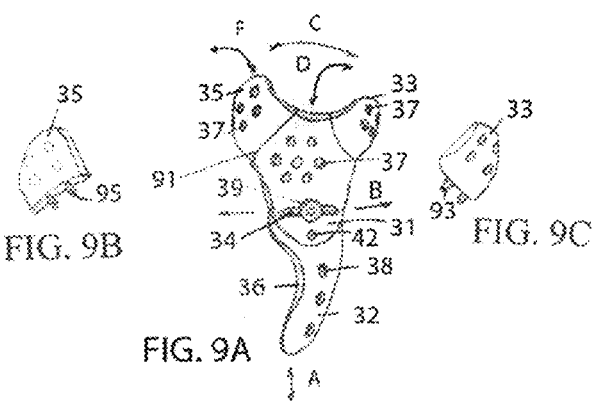

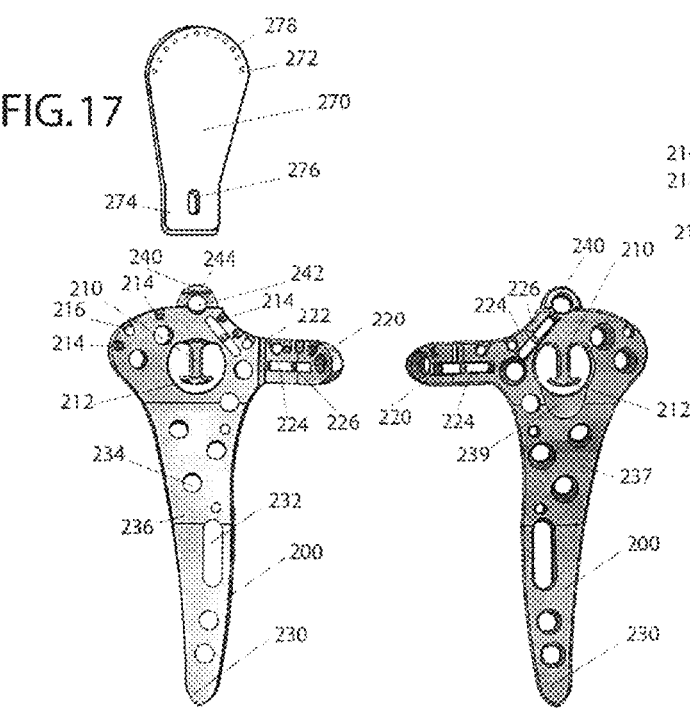
FIG. 17
FIG. 12
FIG. 13
FIG. 18
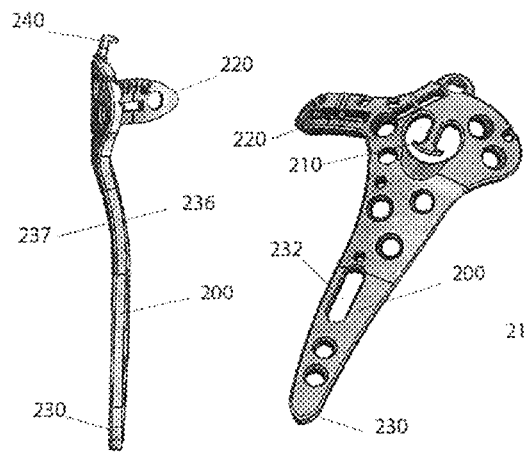
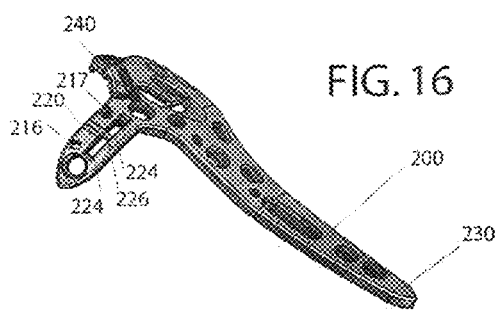
FIG. 14
FIG. 15
FIG. 16

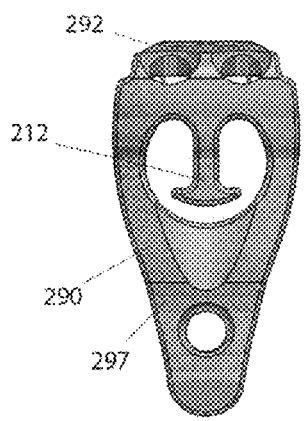
FIG. 19
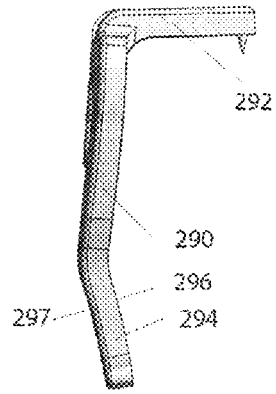
FIG. 20
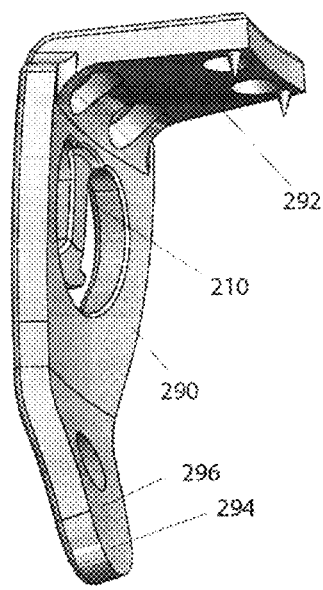
FIG. 21
FIG. 22
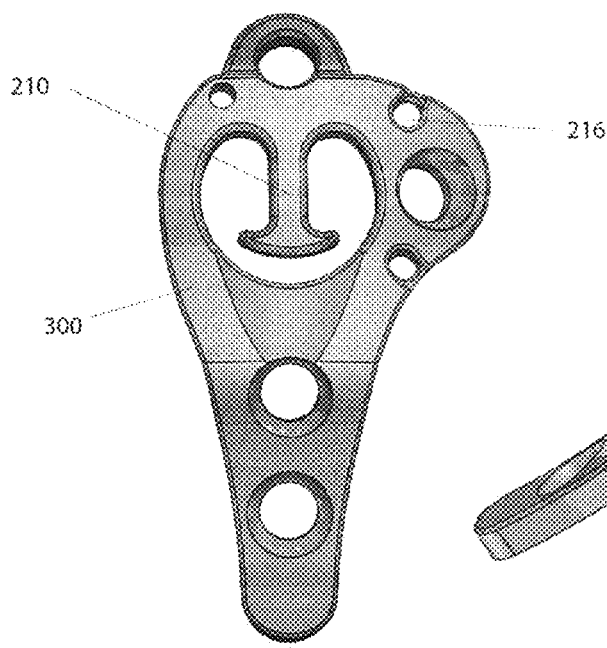
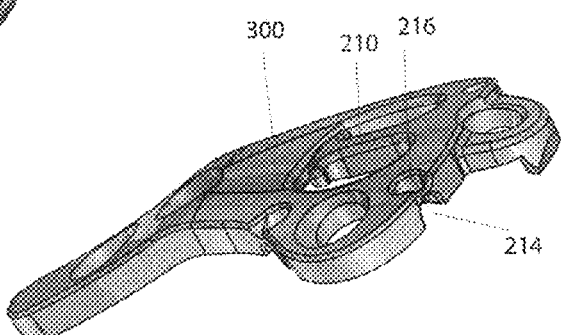
FIG. 23

ANATOMICAL HUMERAL FIXATION SYSTEM AND METHOD

CROSS RELATED APPLICATIONS

This application claims priority to the filing date of U.S. Provisional Appl. No. 61/801,675, which was filed on Mar. 15, 2013, the specification and drawings of which are hereby incorporated by reference.

FIELD OF THE INVENTION

The field relates to implantable medical devices for orthopedics, especially for shoulder fixation devices and methods.

BACKGROUND

FIG. 1 illustrates a known fixture for repairing a fracture of a shoulder that uses a plurality of screws, pins and the like to fix a fractured shoulder bone. U.S. Pat. No. 4,463,753 discloses a bone screw for compressing a fracture. Also, it is known how to make the angle of screws adjustable in a one-piece, solid fixation device, such that the angle of the screws may be adjusted relative to the fixation device. None of the known devices are capable of articulated repositioning of an upper and lower portion of the fixation device.

SUMMARY

An anatomical fixture system and method comprises a lower portion, such as a stem, and an upper portion, such as plate, angled portion or leaf capable of anchoring soft tissues to bone and/or repairing fractures in bone. For example, the anatomical fixture system is used for repairing humeral damage, such as humeral fractures and/or rotator cuff damage caused by torn or severed soft tissues, such as tendons, ligaments and muscles. Screws may be used to fix a lower portion on the bone, and an upper portion may be attached by sutures or screws.

In one example, an anatomical fixation system comprises an upper portion coupled with the greater tuberosity and a lower portion coupled with the lesser tuberosity of the humeral head 11. An arm or wings may be provided. For example the arm or wings may be detachable from the lower portion or the upper portion. A plurality of screws or other fixation devices may be used to secure the lower portion and/or upper portion onto the bone. In one example, a locking mechanism may be provided that adjustably locks the upper portion in relation to the lower portion. For example, the locking mechanism may comprise a bolt capable of coupling the upper portion to the lower portion. For example, the lower portion may be fixed to the bone using one or more screws, and the upper portion may be adjustably coupled to the lower portion by loosely attaching the upper portion to the lower portion with the locking mechanism. Then, the upper portion may be fixed to the humeral head using screws and/or sutures and/or pins as is known in the art.

In one example, the locking mechanism is paired with an adjusting mechanism, such that a fractured head may be repositioned by adjusting the position of the upper portion in relation to the lower portion. Then the locking mechanism may be tightened locking the position of the upper portion in relation to the lower portion of the fixture. The locking mechanism may comprise an element that is bioabsorbable, such that the locking mechanism becomes less effective over time, allowing stress to be accommodated by the anatomical fixture system, initially, and by the bone and soft tissues, eventually, when the bioabsorbable element is partially or fully bioabsorbed. By choosing a bioabsorbable polymer, such as polylactides or other known bioabsorbable polymers, and the dimensions of the bioabsorbable element of the locking mechanism, the system may provide for an extended but not indefinite period for the bone to begin to heal before too much stress is transferred from the system back to the bone. Preferably, the load on the bone and soft tissues is gradually transferred until the bone and soft tissues are healed and become capable of bearing the entire load or a substantial portion of the entire load.

In one example, cut-outs and channels are formed that avoid anatomical features, such as tendons and blood vessels. In one example, a threaded receptacle and a threaded positioner are capable of matingly threading together, such that one portion of the system is angularly displaceable relative to another portion. For example, one portion may be angularly displaced in a plurality of angular directions including arcuately side-to-side and forward-and-back. In one example, the different portions may be translated along a distance and angularly positioned. In yet another example, one portion may be made of a flexible material or a flexible, elastic material capable of freely conforming to anatomical shapes while providing a tensile or tensile elastic stress from a portion where the flexible material is coupled to a rigid fixation system attached to the bone. For example, a lower portion may be a rigid stem fixed to a bone by screws, and a flexible upper portion, such as a leaf, may be coupled to an anchor of the lower portion. The upper portion may be made of a material that readily deforms, such as mesh or patch made of a film or fabric, but the material may be capable of withstanding substantial tensile stresses. In one example, a leaf may be comprised of a film or mesh reinforced by fibers or filaments extending along a length of the material. As is known in the art, such a material may take up substantial tensile stresses without failure, while remaining thin. In one example, such a material comprises a bioabsorbable material capable of being bioabsorbed over time by a human body, when the material is implanted into the body. Such materials are known in the art to include biological tissues and synthetic tissues. A very early bioabsorbable material known in the art is sutures made of cat gut or other such biological tissues. There are many polymers and copolymers capable of being bioabsorbed and the number increases each year.

In one example, a system may be fabricated using 3-D printer technology to provide a custom fit to a patient based on 3-D imaging of the patients humeral bone and imaging of tendons. For example, both the fractured humeral bone and the opposite unfractured humeral bone may be imaged to reconstruct how the system will be formed and adjusted to return the fractured pieces of the humeral bone to a location as close as possible to the anatomical location of the pieces prior to injury. Thus, the system may be anatomically formed to fit the bones and tendons of a particular patients or, alternatively, for a range of patients of similar size and age.

In one example, the fixation system may be positioned further up on the humeral head of the bone, providing significant advantages for angling of the screws that fix the system in place.

In one example, a rack and pinion gear mechanism is provided for repositioning one portion relative to another portion. For example, a slider and a ball may be adjustably engaged for positioning by the rack and pinion gear prior to locking the upper portion in relation to the lower portion with a locking mechanism. Alternatively, an anchor may be provided on a lower portion that engages a portion of an upper portion, such as a leaf, such that the upper portion may be joined to soft tissues, such as tendons, ligaments and muscle, using sutures. For example, the anchor portion may comprise a material taking the shape of an anchor, and the upper portion may comprise a slot capable of being engaged and retained by the anchor, without using any separate locking mechanism. In this example, the anchor and slot prevent the upper portion from being pulled free of the anchor, at least until the portion of the upper portion around the slot is bioabsorbed, for example. In one example, various fixation points (which are not necessarily shaped as an anchor, may be disposed within the lower portion and/or the upper portion of the system. For example, a channel and post extending across a thickness of the channel may be provided, the post providing a location for a suture to be anchored. A post may be formed along an edge comprising through holes through the thickness of one section and surface undercuts extending from an edge to the through holes and forming connecting channels permitting a curved suture needle to extend through the channel and hole to pull a suture through the hole while the section remains fixed to a bone by screws or other fixation devices.

In one example, a greater tuberosity plate is capable of being secured on the greater tuberosity of the humeral bone and comprises a curved inner surface shaped to anatomically fit a humeral head, for example. In another example, a plate comprises an integrally formed extension on one end, angularly extending transversely to a lower portion. For example, the angle may be anatomically arranged at an angle in a range from 40 to 130 degrees to a remaining portion of the integrally formed fixation device. More preferably, the range is 70 to 110 degrees, even more preferably, 80 to 100 degrees. In one example, the extension is perpendicular to another portion of the plate. In another example, a lower portion comprises a stem having an angle corresponding the shape of a humeral bone and humeral greater tuberosity. Typically, the angle is up to 150 degrees with the average humeral neck shaft angle being about 135 degrees.

In another example, a system comprises one or more channels extending into an interior surface. An example is shown of channels in a lower portion of a system, but both the lower and upper portion may have channels. The channels may be used as a way of adjusting the stiffness of portions of the lower and upper portions of the system. For example, a plurality of channels may be formed that intersect at junctions and serve a purpose of adjusting the stiffness of the lower portion, allowing the lower portion to bend in such a way that healing and strength of the bone is improved compared to a strictly rigid lower portion. By allowing some of the stress to be transferred to the bone, channels and bioabsorbable materials may help to provide a more natural callous response during healing.

In the claims, anchor refers to an anchor-shaped or T-shaped structural element, the structural element taking on the shape of an anchor for the purpose of engaging with another element, and "anchor" does not mean the broader definition of a point for anchoring a suture. This specific definition of an anchor is provided herein intentionally and disclaims any other interpretation of the term "anchor" within the claims.

BRIEF DESCRIPTION OF THE DRAWINGS

The following drawings are illustrative examples and do not further limit any claims that may eventually issue.

FIG. 1 illustrates a prior art solid fixation device.

FIG. 2 illustrates the prior art fixation device fixed on a humeral one for fixing a fracture in the humeral bone.

FIG. 3 illustrates an example of an anatomical humeral fixation system as used to repair a humeral fracture.

FIG. 4 illustrates another angle of the example of an anatomical humeral fixation system.

FIG. 5 illustrates another angle of an example without the humerus.

FIG. 6 illustrates a cross section through a portion of an anatomical humeral fixation system.

FIG. 7 illustrates an example of a lower portion of the fixation system.

FIG. 8 illustrates another example of a lower portion of the fixation system having recessed portions for accommodating tendons, such as the bicep tendon.

FIGS. 9A-9C illustrates another example having (9A) a detachable lesser tuberosity wing and (9B) a detachable greater tuberosity wing.

FIG. 12 illustrates another example an anatomical humeral fixation system as used to repair a humeral fracture and/or tears to humeral tendon and/or muscle tissues.

FIG. 13 illustrates an opposite view of the system illustrated in FIG. 12.

FIG. 14 illustrates a side view of the system illustrated in FIG. 12.

FIG. 15 illustrates a perspective view of the system illustrated in FIG. 12.

FIG. 16 illustrates another perspective view of the system illustrated in FIG. 12.

FIG. 17 illustrates a flexible upper portion capable of being coupled with the system of the system illustrated in FIG. 12.

FIG. 18 illustrates a flexible upper portion coupled with the system illustrated in FIG. 12.

FIG. 19 illustrates another example of an anatomical humeral fixation system comprising a rotator cuff plate having a portion extending at a transverse angular direction integrally formed with another portion of the system used for fixing the rotator cuff plate to a bone.

FIG. 20 illustrates a side view of the example illustrated in FIG. 19.

FIG. 21 illustrates an enlarged, perspective view of the example illustrated in FIG. 1

FIG. 22 illustrates yet another example of an anatomical humeral fixation system comprising a greater tuberosity plate.

FIG. 23 illustrates a perspective view of the example of FIG. 22.

When the same reference characters are used, these labels refer to similar parts in the examples illustrated in the drawings.

DETAILED DESCRIPTION

Figure 10B:
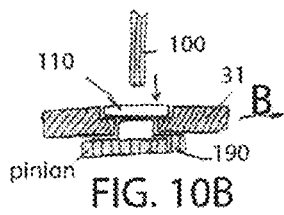
FIGS. 10-10C illustrate a rack and pinion gear for adjusting the position of the upper portion relative to the lower portion.

FIG. 1 illustrates a prior art fixation device 1 for a humeral fracture having an optional plate-like pin 2 and screws 4, 5, 6 and pins 3,7 for fixing the fixture onto the humeral bone. FIG. 2 shows how the fixation device is disposed on the humerus. The device 1 must be disposed on the humeral shaft 10 at a location far from the humeral head 11, and sutures 8 must be used to connect tendons and the like to the fixture 1.

In contrast, an anatomical fixture system 30 and method disposes an upper portion 31 in contact with the greater tuberosity 12 and lesser tuberosity of the humeral head 11 using wings 33, 35. A plurality of screws 37 with locking threads may be inserted through the upper portion 31 and into the bone below the fixture, as is known in the art. A locking mechanism 39 may comprise a bolt capable of coupling the upper portion 31 to the lower portion 32. For example, the lower portion 32 may be fixed to the bone using one or more screws 38, and the upper portion may be adjustably coupled to the lower portion by loosely attaching the upper portion 31 to the lower portion 32 with the locking mechanism 39 loosely fit through a slot 34 in the upper portion. Then, the upper portion may be fixed to the humeral head 11 using screws and/or pins as is known in the art. Subsequently, the head 11 may be repositioned by adjusting the position of the upper portion in relation to the lower portion, and then the locking mechanism 39 may be tightened locking the position of the upper portion in relation to the lower portion of the fixture.

In FIG. 4, a cut-out 36 is illustrated that avoids a tendon disposed on the humeral bone 10. In addition, a threaded receptacle 41 and a threaded positioner 42 capable of matingly threading into the receptacle are shown. The positioner 42 is an example of a mechanism for adjusting an angle D of the upper portion 31 in relation to the lower portion 32. FIG. 5 illustrates some of the displacement A, B and angles C,D that are adjustable using the locking mechanism 39 and the adjusting mechanism positioner 42 of the system together with the slot 34.

FIG. 6 illustrates a cross section along line B of FIG. 5, which together illustrate one example of an adjusting mechanism for adjusting the displacement of the upper portion 31 and the lower portion 32 in an up and down direction A. The locking mechanism 39 in this example is threadingly engaged with a slider 71 that is slidingly engaged in a slot 76. That extends from a slit 74 through at least an upper surface of an engagement portion 82 of the lower portion 32 of the system 30. The slit 74 provides an opening 84 on the surface of the engagement portion 82 of the lower portion 32. FIG. 8 illustrates a recessed portion 86 for the biceps tendon that fits under the anatomically shaped lower surface of the lower portion 32, for example. In one example, the system may be fabricated using 3-D printer technology to provide a custom fit to a patient based on 3-D imaging of the patients humeral bone and imaging of tendons. For example, both the fractured humeral bone and the opposite unfractured humeral bone may be imaged to reconstruct how the system will be formed and adjusted to return the fractured pieces of the humeral bone to a location as close as possible to the anatomical location of the pieces prior to injury. Contact surfaces 73, 75, 79, 89 may be prepared in a way that causes these surface to be locked in place once the locking mechanism 39 is tightened, such as by fitting a tool into a correspondingly shaped recess 72 in the locking mechanism 39.

Thus, the system may be anatomically formed to fit the bones and tendons of a particular patients or, alternatively, for a range of patients of similar size and age. One advantage is that the upper portion may be positioned further up on the humeral head of the bone. This provides significant advantages for angling of the screws that fix the system in place, especially when the wings 33, 35 are used. In one example, as illustrated in FIGS. 9A-9C, for example, the wings 33, 35 are detachable. For example, pins 93, 95 may be used to attach the wings 33, 35, respectively. Alternatively, score lines 91 may be provided that allow the wings to be removed by bending the wings with a removal tool, for example. In one example, the wings may be angularly adjustable in an angular direction F.

Figure 10C:
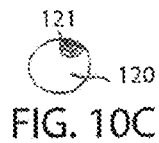
Figure 10:
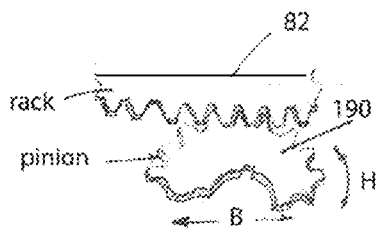
Figure 10A:
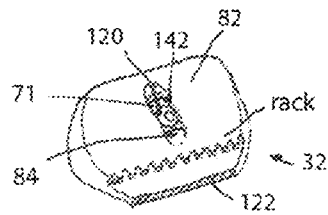

In one example, repositioning of the upper portion relative to the lower portion may be assisted by an adjusting mechanism as illustrated in the exploded view of FIGS. 10-10C, for example. A tool 100 may be used to rotate a gear 101 by inserting the tool in a recess in the gear, for example. For example, the gear comprise a pinion capable of engaging a rack for translating the rack in direction B compared to the pinion, which is rotated in direction H, for example. FIG. 10A illustrates a partial view of the lower portion and how a rack may be integrated into the engagement portion 82 of the lower portion 32, for example. The cross section 122 illustrates a recess formed for providing the teeth of the rack, as illustrated. The opening 84 shows the slider 71 and a ball 120 adjustably engaged within the slider 71. A detailed view of an example of a ball 120 shows a threaded recess 121, which may be capable of being threadingly engaged with the locking mechanism 39, for example.

Figure 11:
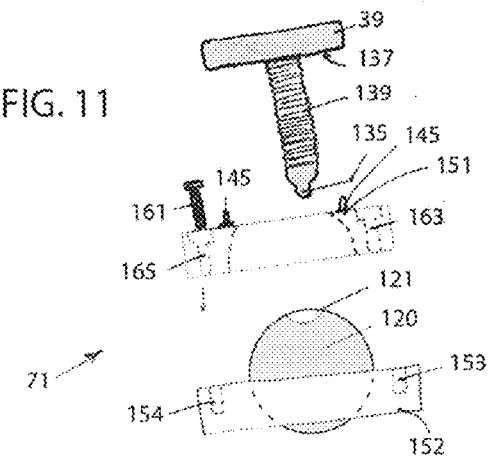
FIG. 11 illustrates a mechanism for adjusting the angle of the upper portion relative to the lower portion with a plurality of angular degrees of freedom.

FIG. 11 illustrates an example of a slider 71 that is comprised of a ball 120 contained in a recess between two halves 151, 152 of the slider 71. These two halves may be joined together by fasteners 161, 163, 165, 153, 154 or may be bonded, welded, brazed, fitted, or otherwise joined one to the other. The slider 71 may have a raised surface 145, which may be used as a guide and/or locking mechanism, by extending slightly above the surface of the lower portion 32. The locking mechanism 39 may have a tip 135 capable of orienting the ball 121 for proper threading with the mechanism, for example. The threads 139 may be selected to avoid cross threading and stripping, for example. The underside 137 of the head of the locking mechanism 39 may be provided with a locking surface, such as by providing roughness or surface features capable of locking the underside to a corresponding contact surface.

The features illustrated in the drawings may be combined and modified to provide for angular and translational displacement of the upper portion in relation to the lower portion of the system giving many degrees of freedom in repositioning the fractured pieces of bone. For example, a rack and pinion gear may be provided to create compression on a fracture in bone during repositioning of the portions of the system, such as up and down direction A, for example. Alternatively, a set screw 68 or other mechanism may be used to adjust the position of the slider in the slit illustrated in FIG. 6. Various combinations of the illustrated features are within the scope of the inventions disclosed.

FIGS. 12-18 illustrate another example of an anatomical humeral fixation system as used to repair a humeral fracture and/or tears to humeral tendon and/or muscle tissues. The anatomical humeral fixation system 200 of FIG. 12 may be used to repair a humeral fracture and/or tears to humeral tendon and/or muscle tissues. An one-piece, integrated structure is shown comprising a stem 230, an anchor portion 210, and eyelet 240 and an arm 220. In the example, the stem comprises a narrow distal end, a widening mid-portion and a flared head portion. Various holes 234 and slots 232 extend through the thickness of the stem 230. The anchor portion 210 is formed within an aperture 250 of the flared head portion of the stem 230. The anchor portion 210 comprises an anchor 212 having an elongated portion 252. The illustration of FIG. 12 shows an inner surface 236 that faces a bone 10, when the system is secured to the bone 10 by screws 4, 5, 6 or other fixation devices, as known in the art. Various fixation points are located within the stem 230 or the arm 220 extending outwardly from the stem 230. For example, a channel 224 and post 226 may be utilized as a suture anchor, or a post may be formed along an edge by holes 216 and surface undercuts 214 forming connecting channels permitting a curved suture needle to fit under the head portion, even when the stem 230 is already fixed to a bone 10 using screws 3, 4, 5. The arm portion 220 may be made detachable from the stem 230 by providing a score line 222 or other weakness that results in a breakaway arm.

The opposite surface 237 of the stem is illustrated in FIG. 13. A recessed portion 239 allows an end portion 274 or tongue of a mesh or patch, such as the flexible leaf 270 illustrated in FIGS. 17 and 18, even when the stem 230 is fixed to a bone 10 with screws 4, 5, 6. In the example in FIG. 17, a leaf 270 comprises a hole, slit or slot 276 capable of being fit over the anchor 212 of the anchor portion 210. The leaf 270 of FIG. 17 comprises an end portion 274 with a slot 276 and a flared end 272 having holes 278 punched or formed within the flared end 272. FIG. 18 illustrates an example of how the leaf 270 is coupled with the anchor portion 210, 212 of the stem 230. The arm portion 210 has a curvature, as best shown in FIGS. 15 and 16, such that the arm portion 220 anatomically fits a portion of the humeral bone 10. Also, the stem 230 has a curvature such that the stem 230 anatomically fits a portion of the humeral bone 10, as best shown in FIG. 14.

FIGS. 19-21 illustrate another example of an anatomical humeral fixation system comprising a rotator cuff plate 290 having an angled portion 292 with teeth extending from a lower face of the angled portion 292, and having screw holes at the vertex, on the stem 294 and on the angled portion 292. The angled portion 292 extends substantially transversely, at a transverse angular direction, such as a right angle, and is integrally formed with a stem 294. An outer surface 297 faces away from a bone when fixed on the bone. An inner face 296 has a curved surface anatomically shaped for fitting on and over the top of a humeral head. For example, the plate 290 may be fixed on the humeral head by pulling a torn tendon or other soft tissue over the angled portion 292 and biting the teeth into the greater tuberosity of the humeral head at a soft tissue attachment region. A leaf 270 or other flexible mesh or patch may be attached to the anchor portion 210, 212 of the plate 290, and sutures may be used to couple the flared end 272 to the soft tissue.

In one example, the material of the leaf 270 and/or the stem 230 is made of a bioabsorbable material, such as a polylactate or other bioabsorbably prepared polymer. Alternatively, the leaf 270 may be a mesh having an elasticity or visco-elasticity that takes up some or all of the load on the soft tissue, initially, and takes up less stress over time, as the leaf 270 stretches over time, such as by creep or viscoelastic/visco-plastic flow. In another example, the stem is made of a permanent solid, such as by 3-D printing from a polymer, capable of being shaped according to an image of a patients bone, such as a CT-scan or other three dimensional scan of a patient's skeletal and soft tissue structures. In one example, the stem 230 is formed, cast or machined of a biocompatible metal, such as a steel or titanium alloy.

In FIG. 22, an anatomical humeral fixation system comprises a greater tuberosity plate 300, capable of being secured on the greater tuberosity of the humeral bone, for example. FIG. 23 shows a perspective view illustrating, together with FIG. 22, some of the same elements of the system illustrated in FIGS. 12-21, and having a curved inner surface shaped to anatomically fit a humeral head, for example.

Figures 24, 25:
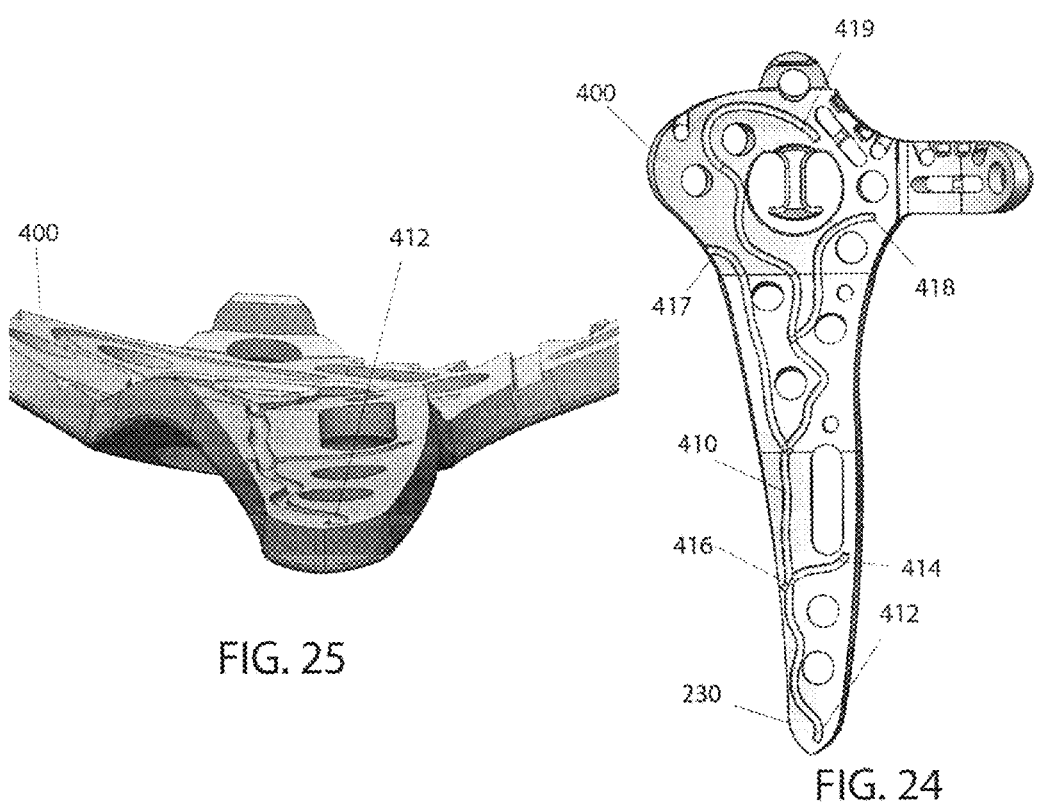
FIG. 24 illustrates another example of an anatomical humeral fixation system showing channels formed in an interior surface.
FIG. 25 illustrates a partial perspective view of one end of the system showing a depth of a channel and junctions where channels intersect.

In another example, FIG. 24 shows a stem 230 comprising channels 410 formed in an interior surface 236 of the stem 230. FIG. 25 illustrates an example of a depth and cross junctions of the channels 410. The channels 410 may have branches 412, 414, 416, 417, 418, 419 extending from junctions 416, for example. For example, the channels 410 may be provided to accommodate anatomical features or may be provided to weaken certain portions of the stem 230 to provide greater deformability or flexibility of the stem 230, such that the stem 230 does not remove all of the stress from a bone. By allowing some of the stress to be transferred to the bone, the channels 410 may help to provide a more natural callous response. If combined with a bioabsorbable material, the channels 410 may provide for an engineered transfer of load from the stem 230 to the bone and soft tissues over time.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. An anatomical fixation system for repairing damage to soft tissues, bone or soft tissues and bone, comprising:
   a one piece stem having a head portion and a distal end, the head portion having an anchor portion extending into aperture, the anchor portion having an elongated portion, the stem having an inner surface adapted for mounting to the bone; and
   a leaf having one end having a slot and an opposite end, the opposite end adapted to couple to the soft tissue, such that the stem and the leaf are cooperatively engaged and soft tissues coupled to the upper portion are retained in place relative to bone coupled to the stem, wherein the anchor prevents translational motion, angular rotation or both translational motion and angular rotation of the leaf relative to the stem in at least in one translational or angular direction.

2. The system of claim 1, wherein the leaf is comprised of a bioabsorbable material.

3. The system of claim 1, wherein the other end comprises a plurality of holes for use in coupling the flared end to soft tissues using sutures retained by a hole.

4. The system of claim 1, wherein the stem has an anatomical shape of the bone and comprising an arm extending outwardly from a side of the stem, the arm being integrally formed with the stem and being detachably connected to the stem such that the arm breaks off of a remainder of the stem at a score line between the remainder of the stem and the arm.

5. The system of claim 1, wherein the lower portion comprises a stem and an angled portion extending transversely to the stem.

6. The system of claim 1, wherein the leaf comprises a slot in one end and a flared end opposite of the one end with the slot.

7. The system of claim 1, further comprising suture attachment elements integrally formed as posts within the lower portion or the upper portion.

8. The system of claim 7, wherein the posts are formed in channels.

9. The system of claim 7, wherein the posts are formed by holes and surface cut-outs on an edge of the lower portion or the upper portion.

10. The system of claim 1, wherein a surface of a stem or leaf has one or more channels extending into an interior surface.

11. An anatomical fixation system for repairing damage to soft tissues, bone or soft tissues and bone, comprising:
- a one piece stem having a head portion, the head portion having an anchor portion and an arm extending outwardly from the head portion of the stem, the arm angularly extending transversely to the stem at an angle in the range from 40 to 130°, the stem having an inner surface adapted for mounting to the bone; and
- a leaf having one end having a slot and an opposite end, the opposite end adapted to couple to the soft tissue, such that the stem and the leaf are cooperatively engaged and soft tissues coupled to the upper portion are retained in place relative to bone coupled to the stem, wherein the anchor prevents translation motion, angular rotation or both translation motion and angular rotation of the leaf relative to the stem in an at least in one translational or angular direction.

12. The system of claim 11 wherein the arm having a score line for detaching a distal portion of the arm.

* * * * *